United States Patent
Natarajan et al.

(10) Patent No.: US 7,908,906 B2
(45) Date of Patent: Mar. 22, 2011

(54) FLUIDIC TEST APPARATUS AND METHOD

(75) Inventors: Govindarajan Natarajan, Poughkeepsie, NY (US); Emmanuel Delamarche, Thalwil (CH); Eric A Eckberg, Rochester, MN (US); James N Humenik, LaGrangeville, NY (US); Kathleen A McGroddy-Goetz, Fairfield, CT (US); Scott Partington, Raleigh, NC (US); Christopher F Perrera, Colchester, VT (US); Marco G Trivella, Raleigh, NC (US); Timothy M Wiwel, Raleigh, NC (US)

(73) Assignee: International Business Machines Corporation, Armonk, NY (US)

(*) Notice: Subject to any disclaimer, the term of this patent is extended or adjusted under 35 U.S.C. 154(b) by 1231 days.

(21) Appl. No.: 11/468,089

(22) Filed: Aug. 29, 2006

(65) Prior Publication Data
US 2008/0057569 A1  Mar. 6, 2008

(51) Int. Cl.
*G01N 13/04* (2006.01)
(52) U.S. Cl. ...... 73/64.47; 73/64.56; 422/63; 435/287.1
(58) Field of Classification Search .............. 73/64.47, 73/64.56
See application file for complete search history.

(56) References Cited

U.S. PATENT DOCUMENTS

| 4,269,197 | A | | 5/1981 | Gilbard |
| 4,753,531 | A | * | 6/1988 | Hiratsuka et al. ............. 356/246 |
| 4,996,993 | A | | 3/1991 | York |
| 5,143,080 | A | | 9/1992 | York |
| 5,611,996 | A | * | 3/1997 | Shaw et al. ..................... 422/63 |
| 7,344,679 | B2 | * | 3/2008 | Natarajan et al. ......... 422/82.01 |
| 2004/0036485 | A1 | | 2/2004 | Sullivan |
| 2005/0104606 | A1 | | 5/2005 | Donsky |
| 2005/0120772 | A1 | | 6/2005 | Sullivan et al. |
| 2005/0201895 | A1 | | 9/2005 | Donsky |

FOREIGN PATENT DOCUMENTS

| WO | 2005/076796 A2 | 8/2005 |
| WO | 2005/089207 A2 | 9/2005 |

* cited by examiner

*Primary Examiner* — Daniel S Larkin
(74) *Attorney, Agent, or Firm* — Joseph Petrokaitis; Roberts Mlotkowski Safran & Cole, P.C.

(57) ABSTRACT

An apparatus, system and method for determining the osmolarity of a fluid. The system includes an apparatus having: a chip with a substantially planar top surface; a first circuit portion and a second circuit portion, each having a plurality of redundant electrically conductive lines disposed on the top surface; and a gap disposed between the first circuit portion and the second circuit portion, wherein a circuit is created when a fluid sample bridges the gap and connects the first circuit portion and the second circuit portion.

12 Claims, 8 Drawing Sheets

FLUIDIC TEST APPARATUS AND METHOD

FIELD OF THE INVENTION

The invention generally relates to an apparatus, system and method for measuring the osmolarity of a relatively small volume of fluid, and more particularly to an apparatus, system and method for measuring the osmolarity of human tears.

BACKGROUND OF INVENTION

Dry eye syndrome (DES), also known as keratoconjunctivitis sicca (KCS), is a condition that occurs due to loss of water from the tear film and is one of the most common complaints seen by optometrists. Studies have found that DES is common in about 15% of patients over the age of 50, with prevalence increasing with age. Dry eye in general is caused by any condition that increases tear film evaporation or by any condition that decreases tear production. For example, evaporation may be increased as a result of having larger eyes (i.e., having more surface area for evaporation to occur from). Also, tear production may decrease from any condition that decreases corneal sensation, such as long term contact lens wear, laser eye surgery, trauma to the 5$^{th}$ nerve, and certain viral infections, etc.

The treatment of DES depends on the severity of the condition. Some patients find relief through the use of various artificial tears. Others utilize supplements containing Omega-3. Still others resort to the insertion of punctual plugs to stop the drainage of tears. Effective treatment, however, begins with effective diagnosis.

In order to diagnose DES, it is useful to determine the osmolarity of the tears in the affected eye. Osmolarity is the measure of the concentration of osmotically active species in a solution, and may be quantitatively expressed in osmoles of solute per liter of solution. It is known that when the tear film loses water, salt and protein concentrations increase relative to the amount of water, resulting in increased osmolarity. Therefore, in order to diagnose and treat DES patients, it is desirable for a treating physician to quantify the osmolarity of a sample tear fluid.

Current techniques for measuring osmolarity involve osmotic pressure measurement, freezing point depression analysis, vapor pressure measurement, and electrical resistance measurement. In one approach, an osmometer is used to measure the osmotic pressure exerted by a solution across a semi-permeable membrane. The osmotic pressure can be correlated to the osmolarity of the solution.

In another approach, the osmolarity of a sample fluid may be determined by an ex vivo technique that involves analyzing the freezing point of the sample fluid. Deviation of the sample fluid freezing point from 0° Celsius is proportional to the solute level in the sample fluid, and is indicative of the osmolarity.

In a further known ex vivo technique, a piece of filter paper is placed under the patient's eyelid to absorb tear fluid. The paper is removed and placed in an apparatus that measures a dew point. The reduction in dew point proportional to that of water can be converted to an osmolarity value.

Lastly, osmolarity may be determined by measuring the conductivity of a fluid sample. The measurement may be made in vivo by placing electrodes under the eyelid. Alternatively, the measurement may be made ex vivo by collecting a sample from the patient and transferring it to a measurement apparatus.

Known techniques for measuring osmolarity, such as those described above, rarely produce accurate or consistent results because they suffer from problems including, for example, inducement of reflex tearing and evaporation of fluid samples. Reflex tearing occurs when the tear glands of the patient are stimulated during tear collection. The stimulation produces extra amounts of liquid, which can lead to false readings (e.g., too high water content). Conversely, when very small samples are taken to avoid reflex tearing, the small samples often immediately begin to evaporate, which can lead to false readings (e.g., too low water content).

Accordingly, there exists a need in the art to overcome the deficiencies and limitations described hereinabove.

SUMMARY OF THE INVENTION

In a first aspect of the invention, an apparatus for determining the osmolarity of a fluid comprises: a chip with a substantially planar top surface; a first circuit portion and a second circuit portion, each comprising a plurality of redundant electrically conductive lines disposed on the top surface; and a gap disposed between the first circuit portion and the second circuit portion, wherein a circuit is created when a fluid sample bridges the gap and connects the first circuit portion and the second circuit portion.

In a second aspect of the invention, a system for determining the osmolarity of a fluid comprises: a holder having a substantially planar layer, a receiving portion disposed above the layer, at least one shelf disposed below the layer, and a hole within a perimeter of the receiving portion and extending through the layer; and a guide having a through hole and an external shape substantially corresponding to an internal shape of the receiving portion, wherein the hole and through hole are aligned with each other, and are arranged to be aligned with a test site, when the guide is received in the receiving portion.

In a third aspect of the invention, a method for determining the osmolarity of a fluid comprises: providing a holder having a substantially planar layer, a receiving portion disposed above the layer, at least one shelf disposed below the layer, and a hole within a perimeter of the receiving portion and extending through the layer, wherein the holder is structured and arranged to receive a chip having a test site for receiving a sample of the fluid.

DETAILED DESCRIPTION OF EMBODIMENTS OF THE INVENTION

The invention is directed to a system and method for determining the osmolarity of fluids, such as, for example, human tears. According to the invention, the osmolarity of a fluid can be determined in a clinically feasible manner, on a nanoliter scale, and with the capability for reduced evaporation, by measuring at least one electrical property (e.g., resistance, conductivity, etc.) of the fluid. In this manner, implementations of the invention may be used for providing accurate and consistent osmolarity measurements, thereby facilitating the diagnosis and treatment of pathological conditions.

Figure 1:
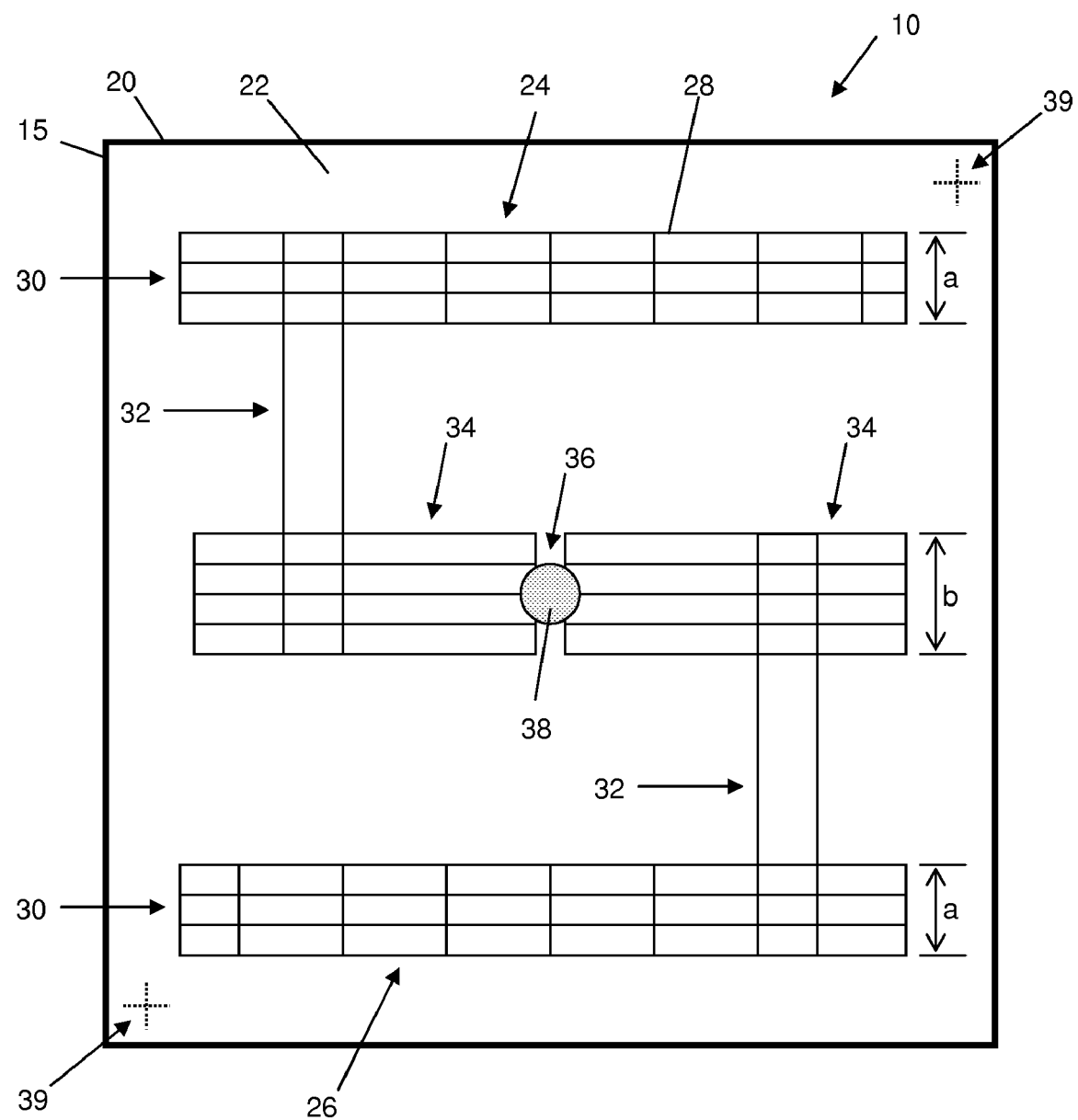
FIG. 1 shows a test chip according to aspects of the invention.

FIG. 1 shows a chip 10, according to implementations of the invention. The chip 10 is provided with at least two circuit portions that, when connected by a fluid, create a single circuit that can be used for determining electrical properties (e.g., resistance, conductivity) of the fluid. The osmolarity of the fluid may then be obtained from known correlation to the determined electrical properties.

Chip 10 has a first side edge 15, second side edge 20, and top surface 22. The chip 10 may be structured and arranged in any suitable size, and may be composed of any suitable material. In embodiments, the chip 10 is composed of a layered structure (for example, a ceramic laminate structure formed by stacking and sintering multiple personalized layers) in which the first side edge 15 and second side edge 20 are each 7 millimeters in length. The chip 10 may, for example, comprise six layers of glass ceramic, each layer being composed of a mixture of silica, alumina, magnesia, and binder (e.g., organic binder).

In the implementation shown in FIG. 1, two circuit portions 24, 26 are disposed on the top surface 22 of the chip 10. Each circuit portion 24, 26 comprises plural lines 28 of electrically conductive material. The lines 28 of each circuit portion 24, 26 are arranged to form an electrode area 30, bridge area 32, and test site area 34. In embodiments, a width "a" of the electrode area may be about 1.5 millimeters, and a width "b" of the test site area may be about 2.0 millimeters. The respective test site areas 34 are separated by a gap 36 of, for example, less than 100 microns. In embodiments, the gap is between 30 and 50 microns. The gap 36 constitutes a test site. When a fluid sample 38, such as a tear drop, is placed across the gap 36 (i.e., test site), the two circuit portions 24, 26 are connected to form one circuit, and electrical properties (e.g., resistance, conductance) of the fluid may be determined as described below. Additionally, the top surface 22 of the chip may comprise alignment markings 39, described below.

The lines 28 of electrically conductive material may be composed of any suitable material, such as, for example, gold, silver, copper, nickel, platinum, etc., and composites thereof. In embodiments, the lines 28 are composed of a mixture of copper, nickel, and glass, which provides low electrical resistance and high oxidation resistance. Even more specifically, the electrically conductive material may be, for example, a mixture of about 56% copper, about 14% nickel, and about 30% glass (e.g., glass ceramic) by volume. The lines 28 may be printed or deposited on the top surface 22 in any suitable manner. The use of plural lines provides redundancy that allows the circuit to be completed even if one, or some, of the lines are damaged or broken. Moreover, the use of plural thin lines (rather than thick lines) ensures mechanical integrity of the entire chip 10 during manufacture by avoiding detrimental effects such as sintering shrinkage and/or breakage due to mismatch of coefficient of thermal expansion. The combination of copper-nickel-glass lines printed on a glass ceramic chip provides a relatively rough surface that is hydrophilic (e.g., attracts water), thus eliminating the need for surface finishing required by smooth (e.g., not hydrophilic) devices. In embodiments, individual or multiple chips may be packaged in a protective vacuum-sealed bag.

Figure 2:
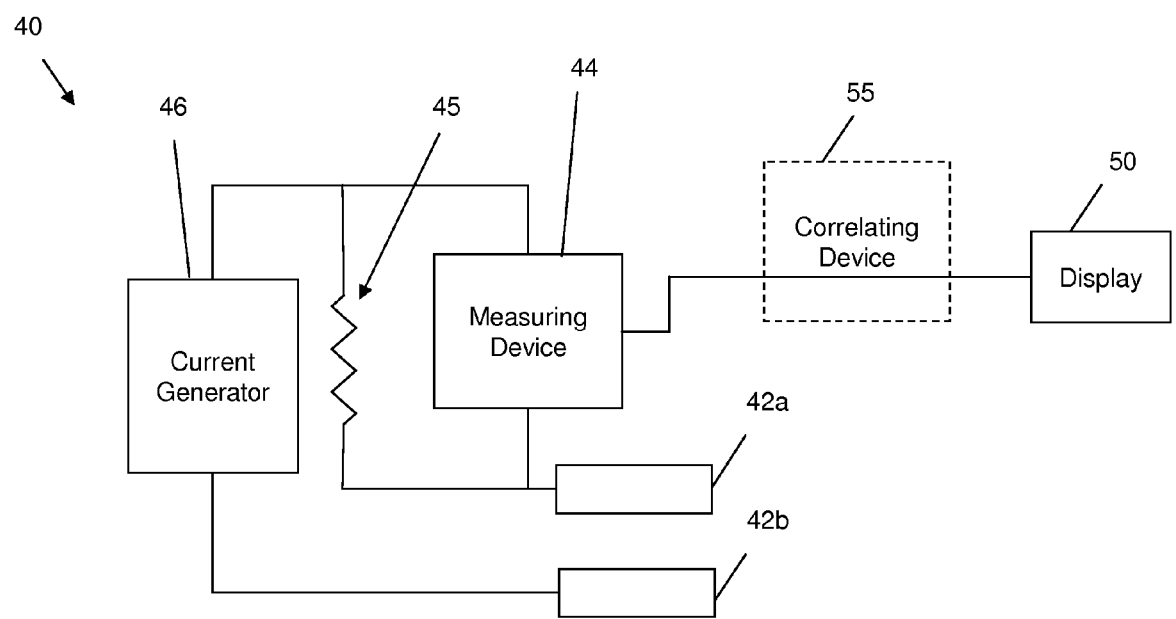
FIG. 2 shows a schematic illustration of a determiner according to aspects of the invention.

FIG. 2 schematically shows a determiner 40 for determining the osmolarity of the fluid sample 38. In embodiments, electrically conductive probes 42a, 42b are connected to the respective electrode areas 30 of the chip 10. For example, a first probe 42a (e.g., pogo probe, alligator clip, etc.) may be laid upon, clipped to, or slidingly brought into contact with a first electrode area 30, and a second probe 42b may similarly be brought into contact with the other electrode area 30. In embodiments, the probes 42a, 42b are also connected to a measuring device 44, bridge 45, and current generator 46. For example, the measuring device 44 may comprise an rms voltmeter, the bridge 45 may comprise a 100 Kohm resistor, and the current generator 46 may comprise a signal generator. When the fluid sample 38 is placed across the gap 36 and closes the circuit, a current, such as, for example, a 100 kHz sinusoidal signal from the generator 46, can be applied to the circuit, and at least one electrical property of the fluid may be determined, as will be understood by those of skill in the art. Certain electrical properties (e.g., conductivity, resistance) of the fluid are directly related to the ion concentration of the fluid in a known manner. Because the ion concentration is related to the osmolarity of the fluid, the osmolarity may be determined from the at least one measured electrical property.

In embodiments, the determiner 40 comprises a display 50 that displays the measured value from the measuring device 44. For example, the display 50 may comprise an LCD display that displays a numerical value that corresponds to the measured electrical property of the fluid. A user may utilize a reference chart, based upon known correlation between the measured electrical property and the osmolarity, to convert the displayed numerical value to an osmolarity value. Optionally, a correlating device 55 that automatically correlates the measured electrical property to the osmolarity may be disposed between the measuring device 44 and the display 50. The correlating device 55 may comprise, for example, a computer processor that receives the value of the measured electrical property, converts the value of the measured electrical property to an osmolarity value by accessing look-up tables or correlation equations, and outputs the osmolarity value to the display.

Figure 3:
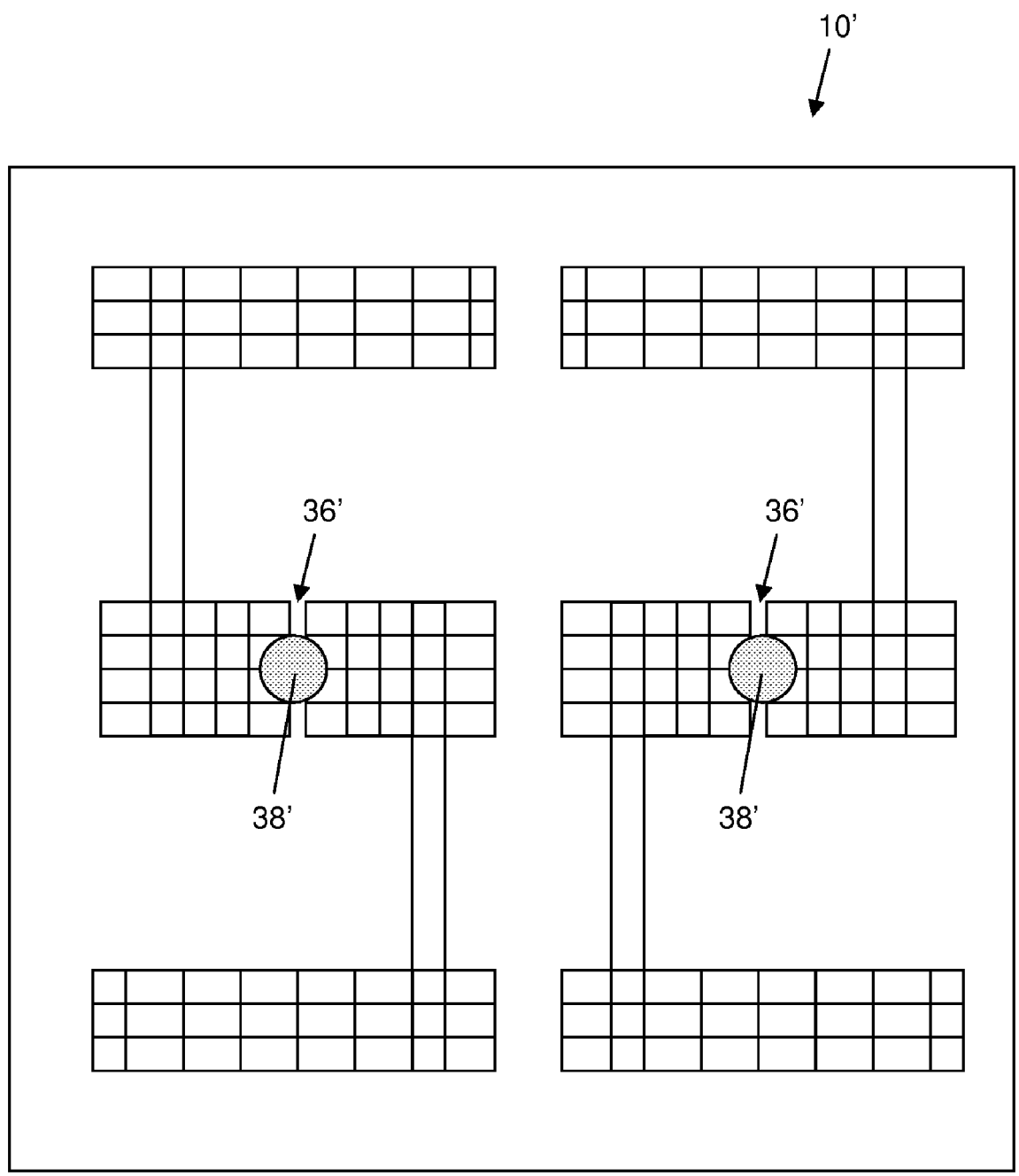
FIG. 3 shows a test chip according to aspects of the invention.
Figure 4:
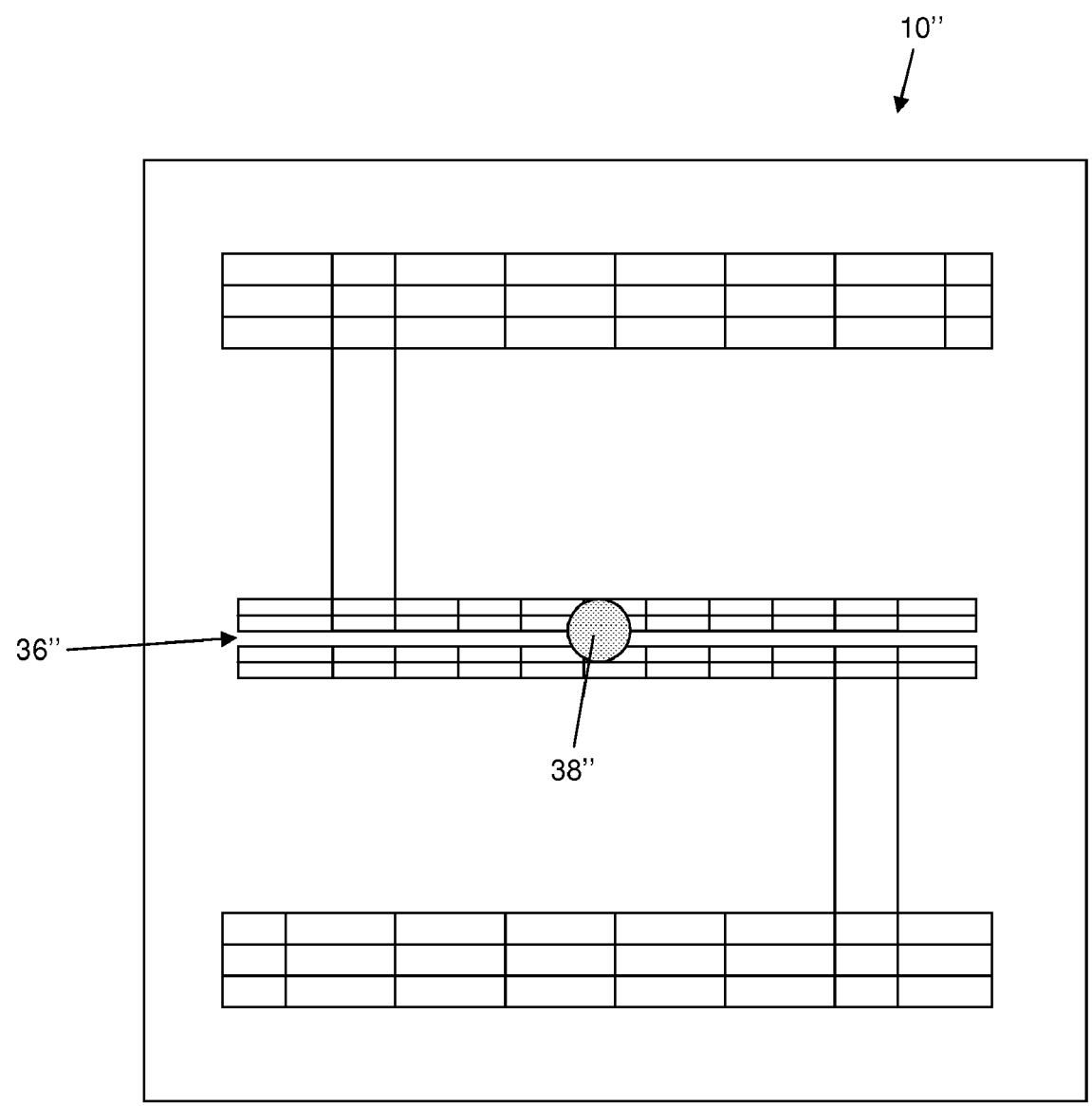
FIG. 4 shows a test chip according to aspects of the invention.

FIGS. 3 and 4 illustrate alternative embodiments of the test chip. In the embodiment shown in FIG. 3, the top surface of the chip 10' has two circuits, each having respective circuit portions separated by a gap 36' across which a fluid sample 38' may be placed. In this manner, multiple test sites may be located on the same side of the chip, thereby allowing the same chip to be used for making multiple determinations. Although two circuits (and, therefore, two test sites) are shown on the top surface of the chip in FIG. 3, any number and configuration of circuits could be arranged on the top surface. Furthermore, circuits (and, therefore, test sites) could be disposed on both the top surface (as shown) and the bottom surface (not shown) of the same chip.

Moreover, as shown in FIG. 4, a gap 36" may run along the length of the respective test site areas (instead of transverse to the length of the respective test site areas, as previously shown). In this manner, a larger test site may be provided, thereby reducing the degree of precision required when placing the fluid sample 38" on the chip 10".

Figure 5A:
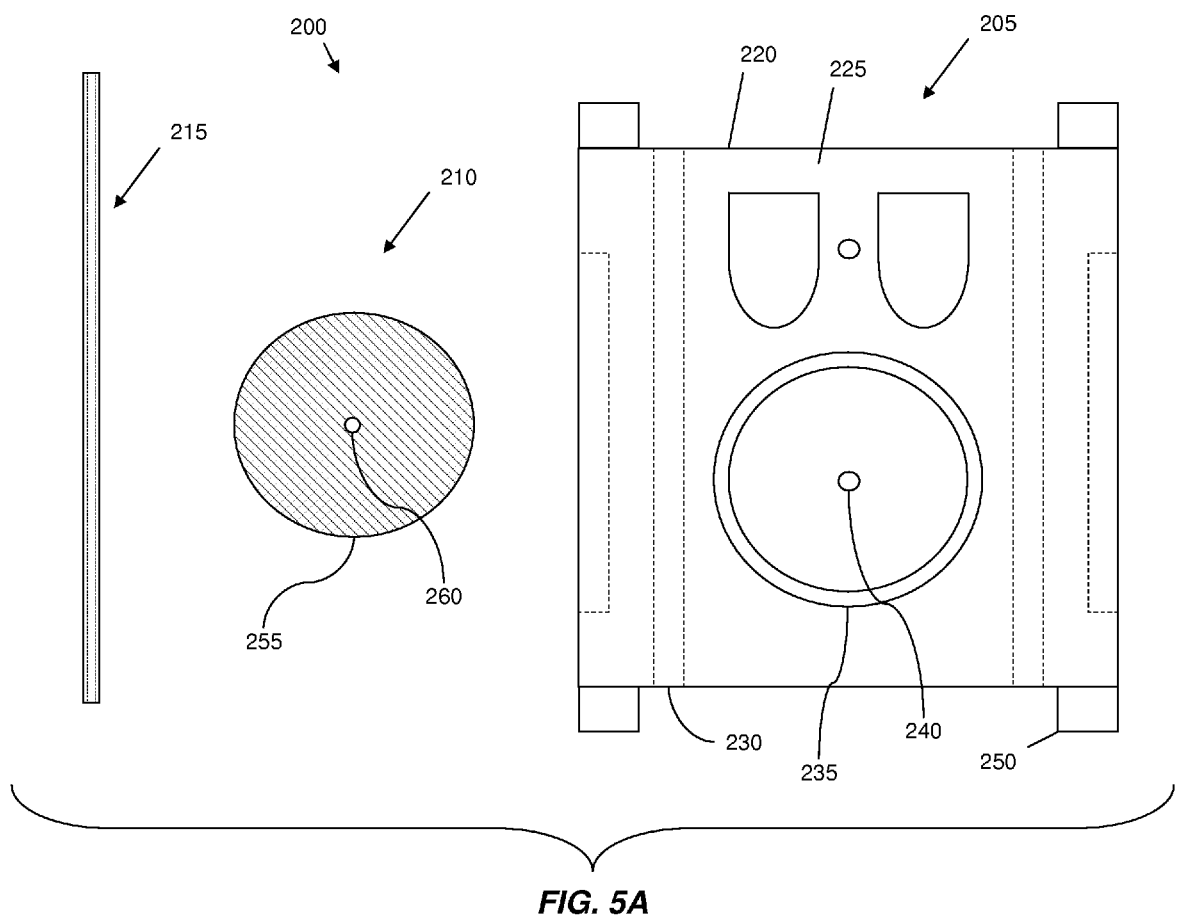
FIG. 5A shows a system according to aspects of the invention.

FIG. 5A shows a system according to aspects of the invention. In embodiments, the system 200 comprises a holder 205, a guide 210, and a collector 215. The system 200 may also include any chip as described above. In this manner, the system may be used to determine the osmolarity of a fluid.

In embodiments, the holder 205 includes a stand 220 that is structured and arranged to receive the chip 10. The stand 220 comprises, for example, a generally planar layer 225. Disposed below the layer 225 is a shelf 230 that is capable of slidingly receiving a chip 10. Disposed above the layer 225 is a receiving structure 235. In the implementation shown in FIG. 5A, the receiving structure 235 is a generally cylindrical wall with a centrally disposed bore. A hole 240 is disposed within the receiving structure and extends through the layer 225. The holder 205 aligns the chip 10 to the hole 240 with features that pick up datums of the chip (e.g., external chips edges 15 and 20, optical alignment markings 39, etc.). The holder 205 may also include projections 250 for aligning the holder with other equipment. The holder 205 may be made of any appropriate material. In embodiments, the holder 205 is composed of plastic material and is formed by injection molding.

The system shown in FIG. 5A also includes guide 210. The guide 210 comprises a body 255 having an external shape that corresponds to the internal shape of the receiving structure 235, such that the guide 210 may be snugly inserted into the receiving structure 235. A through hole 260 extends through the body 255. When the guide 210 is received in the receiving structure 235, the through hole 260 is aligned with the hole 240 in the layer 225. The body 255 may be made of any appropriate material. In embodiments, the body is composed of a relatively soft elastomer, such as, for example, neoprene, silicone, etc.

Still referring to FIG. 5A, the system also includes a collector 215. In embodiments, the collector 215 comprises a micropipette or a capillary tube, and is used for collecting the fluid sample to be tested. For example, a micropipette can be used to collect a tear from the human eye via capillary action and without inducing reflex tearing, as is known in the art. The collector is sized to fit through the through hole 260 of the guide 210, and also the hole 240 of the holder 205.

The components of the system 200 are designed such that when the chip 10 is disposed in the holder 205, the test site (e.g., gap 36) aligns with the hole 240. Moreover, when the guide 210 is inserted in the receiving structure 235, the through hole 260 is also aligned with the test site. Accordingly, when the collector 215 is inserted into the guide 210, it is also aligned with the test site. In this manner, the system 200 may be used to precisely transfer the fluid sample from the collector 215 to the test site, reducing the chances of the fluid sample being placed on the wrong area of the chip 10 (e.g., not across the gap 36).

Although the holder has been shown and described with a single receiving structure 235 and hole 240, the holder 205 may have multiple receiving structures and holes. That is, the holder 205 may be structured and arranged to have a respective receiving structure 235 and hole 240 aligned with each test site on a chip. Moreover, the shape of the receiving structure is not limited to cylindrical.

Figure 5B:
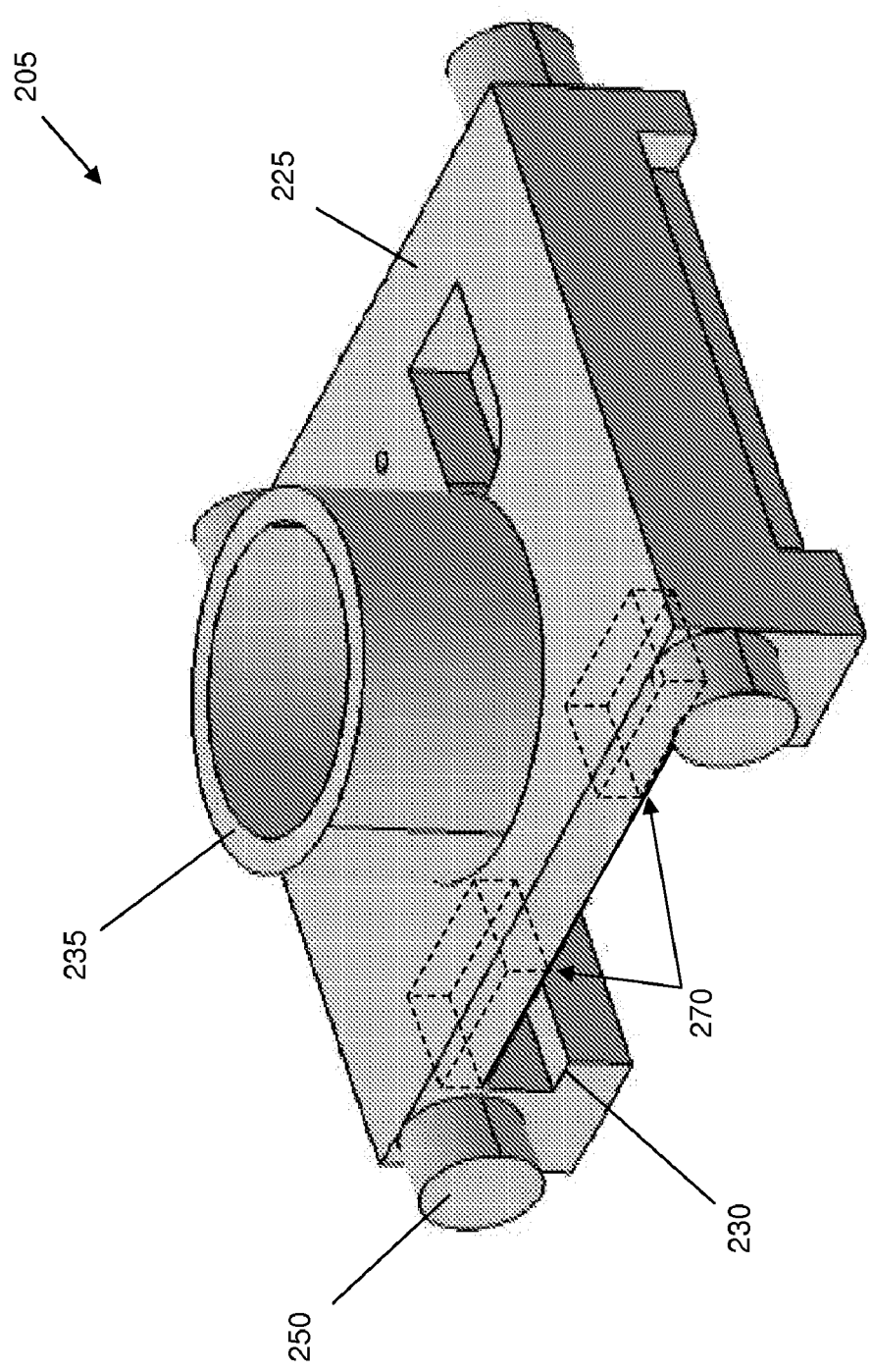
FIG. 5B shows a holder according to aspects of the invention.

In embodiments, the holder 205 comprises electrodes 270 in the vicinity of the shelf 230, as shown in FIG. 5B. The holder 205 and chip 10 may be structured and arranged such that when the chip 10 is held in the holder 205, respective electrodes 270 contact respective electrode areas 30 of the chip 10. The electrodes 270 may, for example, correspond to the probes 42a, 42b of the determiner 40, as described above. The other elements of the determiner 40 may be contained within (e.g., as part of) the holder 205, or may be external to the holder 205. For example, the holder 205 and determiner 40 may be integrated into a single hand-held or desktop device that automatically displays the osmolarity value of a fluid upon insertion of a chip 10 and depositing of a fluid sample onto the test site via the collector 215, as described above.

Method of Use

Figure 6A:
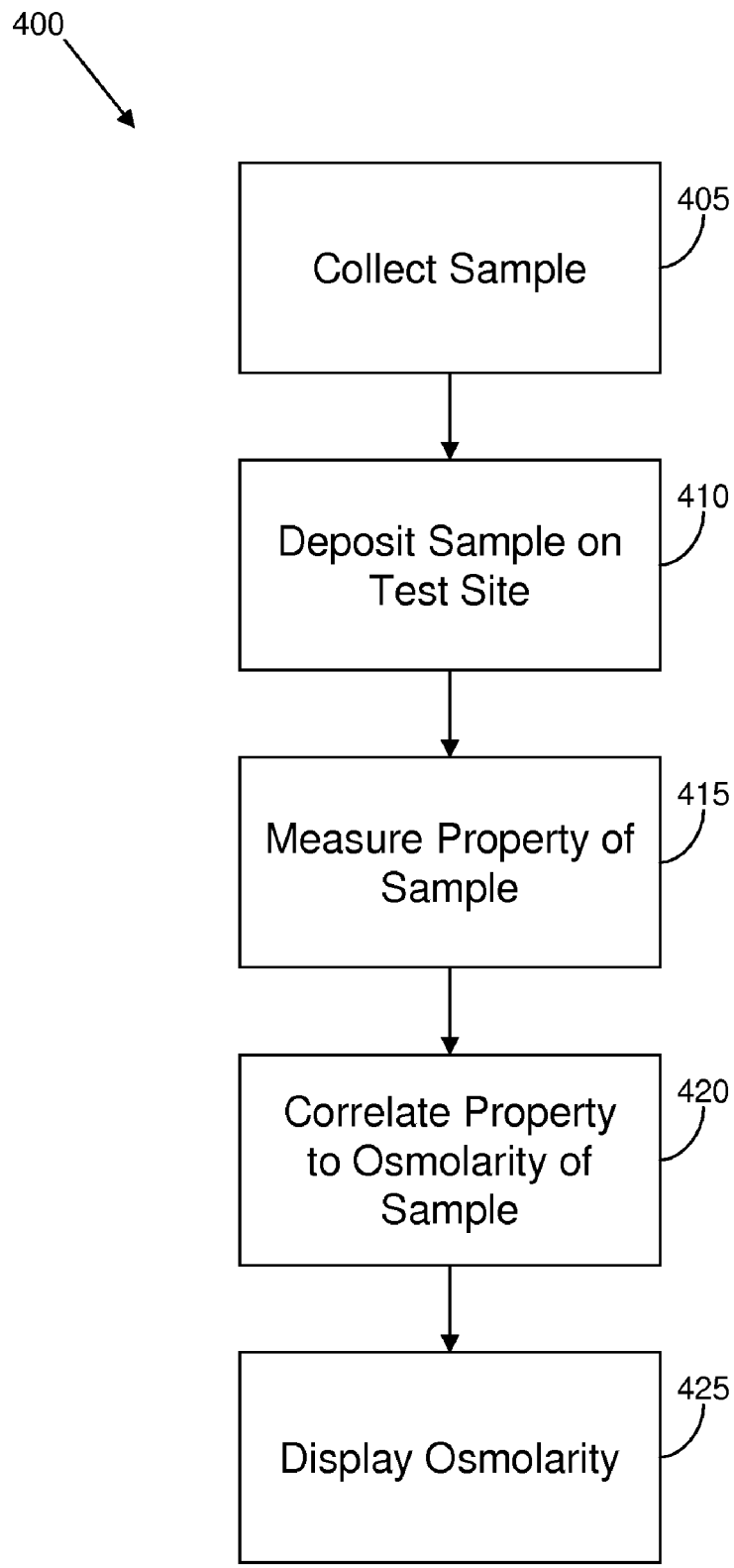
FIGS. 6A and 6B show flow diagrams depicting methods according to aspects of the invention.
Figure 6B:
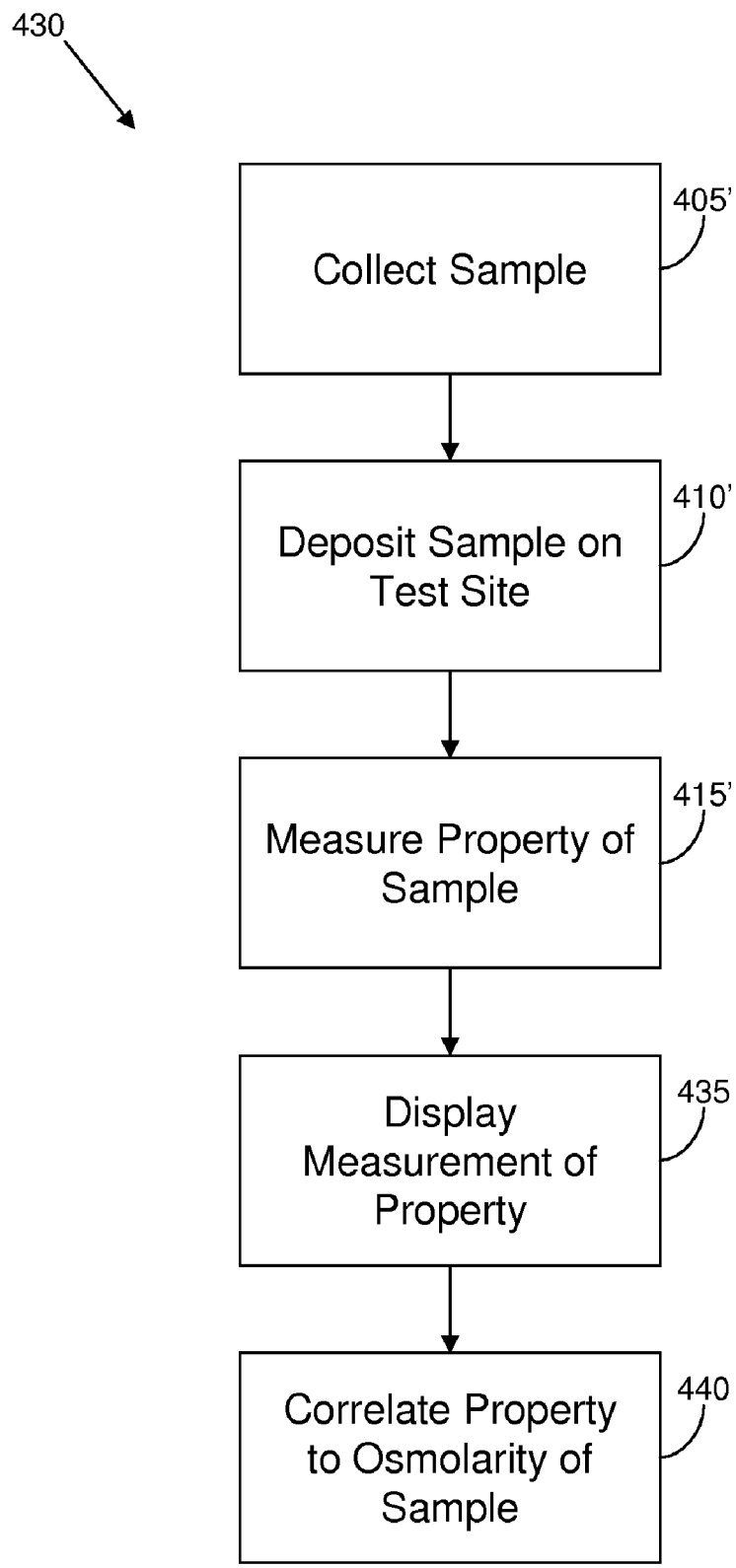

FIGS. 6A and 6B are flow diagrams implementing steps of the invention. FIGS. 6A and 6B may equally represent a high-level block diagram of the invention. Some of the steps of FIGS. 6A and 6B may be implemented and executed from either a server, in a client server relationship, or they may run on a user workstation with operative information conveyed to the user workstation to create the navigation outlined above. Additionally, aspects of the invention can take the form of an entirely hardware embodiment, an entirely software embodiment or an embodiment containing both hardware and software elements.

In an embodiment, aspects of the invention are implemented in software, which includes but is not limited to firmware, resident software, microcode, etc. Furthermore, aspects of the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

FIG. 6A shows a first method 400 according to a first aspect of the invention. At step 405, a sample of fluid is collected for the purpose of determining the osmolarity of the fluid. The sample may be collected, for example, by using a micropipette or capillary tube to draw fluid (e.g., tear, blood, etc.) from a patient (e.g., human, dog, cat, etc.), as will be understood by those skilled in the art.

At step 410, the sample is deposited onto a test site. In embodiments, this comprises using the previously described system 200 to deposit the sample onto a chip 10 such that the sample bridges the gap 36 on the chip. For example, a chip 10 may be slid onto the shelf 230 of the holder 205, such that the gap 36 is aligned into the hole 240. Then the guide 210 may be inserted into the receiving structure 235. The collector is inserted into the through hole 260 to extend through the hole 240. To avoid damaging the chip 10 and/or collector 215, care should be taken to avoid bringing the collector 215 into contact with the chip 10.

Still referring to step 410, the fluid sample that was collected in the collector 215 at step 405 is expelled from the collector onto the test site. In embodiments, this is accomplished by increasing the air pressure behind the sample held inside the collector. This may be accomplished in any known manner, such as, for example, using an elastic bulb, air pump, air compressor, etc. The increased air pressure pushes the sample out of the collector 215. Since the collector is aligned with the test site, the sample is expelled onto the test site (e.g., across the gap 36, thereby completing the circuit).

At step 415, at least one electrical property of the fluid is measured. In embodiments, this is accomplished using the determiner 40 described above. For example, a current may be applied to the circuit, and the resistance (or conductance) of the fluid may be measured in a known manner.

At step 420, the measured value of the at least one electrical property of the fluid is correlated to an osmolarity value of the fluid. In embodiments, this is accomplished using a microprocessor that applies a look-up table or correlation equation to the value of the measured electrical property.

At step 425, the osmolarity value is displayed. In embodiments, the value is displayed on an LCD, computer screen, or similar display.

FIG. 6B shows a second method 430 according to a second aspect of the invention. The steps 405', 410', and 415' may be performed in a manner similar to steps 405, 410, and 415 of first method 400. However, in the second method 430, the value of the measured property is displayed at step 435 before correlating it to the osmolarity at step 440. For example, the value of the measured property, such as, for example, a voltage that corresponds to the measured property, is displayed at step 435. Then, at step 440, a user manually correlates the value to an osmolarity value by, for example, referring to a written chart. In this way, the second method 430 may be implemented without using an automatic correlating device (e.g., microprocessor).

While the invention has been described with respect to measuring the osmolarity of human tears, the invention is not limited to such applications. The invention can be used with other fluids, such as, for example, blood, urine, sweat, plasma, semen, etc. Moreover, the invention may be used to test the osmolarity fluids from any source (e.g., drinking water), not just those of humans.

While the invention has been described in terms of embodiments, those skilled in the art will recognize that the invention can be practiced with modifications and in the spirit and scope of the appended claims.

What is claimed:

1. A system, comprising:
a holder having a substantially planar layer, a receiving portion disposed above the layer, at least one shelf disposed below the layer, and a hole within a perimeter of the receiving portion and extending through the layer;
a guide having a through hole and an external shape substantially corresponding to an internal shape of the receiving portion, wherein the hole and through hole are aligned with each other and are arranged to be aligned with a test site when the guide is received in the receiving portion;
electrical contact portions disposed adjacent to the at least one shelf, wherein the electrical contact portions are structured and arranged to contact portions of a circuit of a chip that comprises the test site;
a device connected to the electrical contact portions structured and arranged to determine a value of an electrical property of a fluid;
a display connected to the device; and
a collector for collecting a fluid sample, wherein the collector is structured and arranged to extend through the through hole and the hole.

2. A method for determining an osmolarity of a fluid, comprising:
providing a holder having a substantially planar layer, a receiving portion disposed above the layer, at least one shelf disposed below the layer, and a hole within a perimeter of the receiving portion and extending through the layer, wherein the holder is structured and arranged to receive a chip having a test site for receiving a sample of the fluid;
providing a guide having a through hole and an external shape substantially corresponding to an internal shape of the receiving portion; and
providing the chip having the test site,
wherein the holder comprises a first electrical contact portion and a second electrical contact portion disposed adjacent the at least one shelf,
the first electrical contact portion and the second electrical contact portion are arranged to come into contact with the chip,
the first electrical contact portion and the second electrical contact portion are arranged to connect to a device that measures a property of the sample, and
the device is arranged to connect to a display that displays at least one of the measured property and a determined osmolarity, wherein
the determined osmolarity is provided by a correlation method.

3. A system, comprising:
a holder having a substantially planar layer, a receiving portion disposed above the layer, at least one shelf disposed below the layer, and a hole within a perimeter of the receiving portion and extending through the layer;
a guide having a through hole and an external shape substantially corresponding to an internal shape of the receiving portion,
wherein the hole and through hole are aligned with each other, and are arranged to be aligned with a test site, when the guide is received in the receiving portion; and
electrical contact portions disposed adjacent to the at least one shelf.

4. The system of claim 3, wherein the electrical contact portions are structured and arranged to contact portions of a circuit of a chip that comprises the test site.

5. The system of claim 3, wherein:
the at least one shelf comprises a first shelf and a second shelf; and
the electrical contact portions comprise a first electrical contact portion disposed adjacent the first shelf and a second electrical contact portion disposed adjacent the second shelf.

6. The system of claim 3, wherein the electrical contact portions comprise a first electrical contact portion and a second electrical contact portion, and
the system further comprises:
a device connected to the first electrical contact portion and the second electrical contact portion, and structured and arranged to determine a value of an electrical property of a fluid; and
a display connected to the device.

7. A system, comprising:
a holder having a substantially planar layer, a receiving portion disposed above the layer, at least one shelf disposed below the layer, and a hole within a perimeter of the receiving portion and extending through the layer;
a guide having a through hole and an external shape substantially corresponding to an internal shape of the receiving portion,
wherein the hole and through hole are aligned with each other, and are arranged to be aligned with a test site, when the guide is received in the receiving portion; and
a collector for collecting a fluid sample, wherein the collector is structured and arranged to extend through the through hole and the hole.

8. A method, comprising:
providing a holder having a substantially planar layer, a receiving portion disposed above the layer, at least one shelf disposed below the layer, and a hole within a perimeter of the receiving portion and extending through the layer, wherein the holder is structured and arranged to receive a chip having a test site for receiving a sample of a fluid, and wherein the holder further comprises a first electrical contact portion and a second electrical contact portion disposed adjacent the at least one shelf.

9. The method of claim 8, further comprising providing a guide having a through hole and an external shape substantially corresponding to an internal shape of the receiving portion.

10. The method of claim 8, further comprising providing the chip having the test site.

11. The method of claim 8, wherein:
the first electrical contact portion and the second electrical contact portion are arranged to come into contact with the chip,
the first electrical contact portion and the second electrical contact portion are arranged to connect to a device that measures a property of the sample, and
the device is arranged to connect to a display that displays at least one of the measured property and a determined osmolarity wherein the determined osmolarity is provided by a correlation method.

12. A method, comprising:
providing a holder having a substantially planar layer, a receiving portion disposed above the layer, at least one shelf disposed below the layer, and a hole within a perimeter of the receiving portion and extending through the layer,
wherein the holder is structured and arranged to receive a chip having a test site for receiving a sample of a fluid;
providing a guide having a through hole and an external shape substantially corresponding to an internal shape of the receiving portion; and
providing instructions to:
insert the guide into the receiving structure;
collect the sample with a collector;
insert the collector through the through hole and hole; and
expel the sample onto the test site.

* * * * *